United States Patent [19]

Reamer et al.

[11] Patent Number: 5,093,324
[45] Date of Patent: Mar. 3, 1992

[54] THIADIAZOLE ANTIVIRAL AGENTS

[75] Inventors: Marie T. Reamer; Wayne A. Spitzer; Frantz Victor, all of Indianapolis, Ind.

[73] Assignee: Eli Lilly and Company, Indianapolis, Ind.

[21] Appl. No.: 339,033

[22] Filed: Apr. 14, 1989

[51] Int. Cl.$^5$ .................. A61K 31/00; C07H 19/00
[52] U.S. Cl. ........................... 514/43; 536/23
[58] Field of Search .................. 536/23, 29; 514/43

[56] References Cited

U.S. PATENT DOCUMENTS

| | | | |
|---|---|---|---|
| 3,891,762 | 6/1975 | Wakae et al. | 514/363 |
| 3,984,396 | 10/1976 | Witkowski et al. | 536/29 |
| 4,093,624 | 6/1978 | Revankar et al. | 536/23 |
| 4,835,168 | 5/1989 | Paget et al. | 514/363 |

FOREIGN PATENT DOCUMENTS

| | | |
|---|---|---|
| 229501 | 7/1987 | European Pat. Off. . |
| 46-35262 | 10/1971 | Japan . |
| 48-466 | 1/1973 | Japan . |
| 49-07218 | 2/1974 | Japan . |

OTHER PUBLICATIONS

Naik et al., *J. Indian Chem. Soc.*, vol. LX, Jul. 1983, pp. 674–678.
Grant et al., *J. Med. Chem.*, vol. 15, No.1 10, 1972, pp. 1082–1084.
Russo et al., *Farmaco*, Ed. Sci., 1975, 30(12) 1031–1038.
Malinoski et al., *Virology*, 110, 281–291 (1981).
Nelson et al., *Cancer Res.* 37, 182–187 (1977).
Bonina et al., Antimicrobial Agents and Chemotherapy, Dec. 1982, 1067–1069.
Widell et al., *Antiviral Research*, 6, 103–112 (1986).
Chemical Abstracts, 85, 193010q (1976).
Witkowski et al., *J. Med. Chem.*, 15(11), 1150 (1972).
Witkowski et al., *J. Med. Chem.*, 16(8), 935 (1973).

*Primary Examiner*—John W. Rollins
*Assistant Examiner*—James O. Wilson
*Attorney, Agent, or Firm*—Douglas J. Taylor; Leroy Whitaker

[57] ABSTRACT

Ribosylated 2-amino-1,3,4-thiadiazoles having antiviral activity, methods of use and pharmaceutical formulations therefor.

9 Claims, No Drawings

THIADIAZOLE ANTIVIRAL AGENTS

BACKGROUND OF THE INVENTION

Antiviral agents, to date, have not been widely effective as therapeutic agents in the treatment of the various disease states mediated by viruses. The morbidity and mortality caused thereby represents significant impetus for the search for new antiviral agents. The present invention addresses that need and provides new antiviral agents as described in detail hereinafter.

SUMMARY OF THE INVENTION

The present invention is directed to certain 3-ribosylated 2-amino-1,3,4-thiadiazoles of the formula

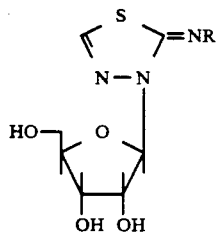

wherein:
R is hydrogen, —CN,

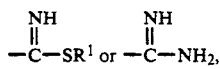

where $R^1$ is $C_1$-$C_6$ alkyl, cyano-$C_1$-$C_4$ alkyl or pyridyl-$C_1$-$C_4$ alkyl, or a pharmaceutically acceptable salt thereof. Also disclosed and claimed herein are antiviral methods and pharmaceutical formulations containing the compounds of formula 1. Such methods include administering to a mammal in need thereof an effective antiviral amount of a compound of formula I as defined above. Similarly, pharmaceutical formulations including an effective amount of a compound of formula I as defined above in association with one or more pharmaceutically acceptable diluents, excipients or carriers are disclosed and claimed.

DETAILED DESCRIPTION OF THE INVENTION

The non-ribosylated form of the 2-amino-1,3,4-thiadiazoles are disclosed in U.S. patent application Ser. No. 07/165,96, now U.S. Pat. No. 4,835,168, which is incorporated herein by reference. Additionally, a published foreign cognate thereof is European Patent Application EP 229,501, which is also incorporated herein by reference.

As used in the definition of formula I, the term "$C_1$-$C_6$ alkyl" refers to straight and branched chain aliphatic radicals of one to six carbon atoms, both inclusive, such as methyl, ethyl, propyl, isopropyl, butyl, sec-butyl, pentyl, isopentyl, hexyl, isohexyl and the like. The term "$C_1$-$C_6$ alkyl" includes within its definition the term "$C_1$-$C_4$ alkyl".

The compounds of the present invention are readily prepared utilizing methodology well known in the art from starting materials which themselves are either commercially available or readily prepared by known techniques. For example, the non-ribosylated 2-amino-1,3,4-thiadiazoles may be prepared as described in the previously mentioned European Patent Application EP229501 as well as by the procedure of Naik et al. in *J. Indian Chem. Soc.*, Vol. LX, 674–678 (July, 1983) and ( Muso et al., *Farmco. Ed. Sci.*, Vol. 30, No. 12, 1031–1038 (1975) both of which are incorporated herein by reference. Compounds of the present invention can be prepared by reacting a 1,3,4-thiadiazol-2-ylthiourea with an alkylating agent of the formula $R^1X$ where $R^1$ is as defined above and X is a leaving group. Suitable leaving groups include chloro, bromo, iodo, as well as sulfonic ester groups such as tosylate and mesylate. Thus, suitable alkylating agents include, for example, an alkyl halide such as methylbromide, or a substituted alkyl halide such as cyanomethyl bromide or 2-pyridylmethyl iodide. The reactions are typically accomplished by mixing approximately equimolar quantities of a 2-thiadiazolylthiourea and an alkylating agent in the presence of a base such as sodium carbonate in an unreactive organic solvent such as dimethylformamide or acetonitrie. The reaction is normally complete within about 16 hours when carried out at about 20° C. to about 50° C. The reaction solvent can be removed by evaporation under reduced pressure if desired. The product is readily purified by routine methods, including crystallization from solvents such as ethanol, ethylacetate or hexane; or by chromatography over solid supports such as silica and the like.

The ribosylation reaction is similarly carried out by known methodologies. See, for example, Revankar et al., *J. Org. Chem.* 39, No. 9 (1974) which is incorporated herein by reference. For example, the 1-bromo derivative of β-d-ribofuranose (or preferably, a derivative with appropriately blocked hydroxyl groups such as 2,3,5-tri-0-acetyl-D-ribosyl bromide) may be reacted with the desired 2-amino-1,3,4-thiadiazole or derivatives thereof (preferably as the salt) in an aprotic solvent such as dimethyformamide (DMF) under an inert atmosphere. The reaction is allowed to proceed at room temperature for about 8 to about 12 hours after which the ribosylated product may be recovered by conventional work-up.

A preferred compound of the present invention is 1,3,4-thiadiazol-2-ylcyanamide-3-β-d-ribofuranose. The non-ribosylated thiadiazole precursor of this preferred compound can be prepared by reacting a carbamidothioic acid ester with an oxidizing agent such as meta-chlorcperbenzoic acid, peracetic acid, sodium peroxide, hydrogen peroxide, ozone, chlorine or the like followed by ribosylation as described above.

The 1,3,4-thiadiazol-2-ylcyanamide can also be prepared by reacting a protected 2-aminothiadiazole derivative, namely 2-imino-3-phenylmethyl-1,3,4-thiadiazole with cyanogen bromide and then removing the protecting group at the 3-position by debenzylation with a Lewis acid, e.g., aluminum chloride. The debenzylation is carried out in an organic solvent such as methylene chloride, toluene or benzene. Preferably, at least 2 equivalents of Lewis acid are used, and more preferably 4 to 8 equivalents are used. The temperature for the reaction is not critical. The debenzylation can be carried out, for example, at from 0° C to 90° C. Room temperature is preferred.

The non-ribosylated cyanamide readily forms pharmaceutically acceptable salts by reaction with organic and inorganic bases such as sodium acetate, calcium carbonate, sodium hydroxide and the like. Some of the compounds of this invention can exist in tautomeric form, all of which are included within the scope of the present invention.

The following examples are provided as a means of illustrating the present invention and are not to be construed as a limitation thereof.

EXAMPLE 1

1,3,4-Thiadiazol-2-ylcyanamide-3-$\beta$-d-ribofuranose triacetate

A. Preparation of [(1,3,4-thiadiazol-2-ylamino)thioxomethyl]carbamic acid, ethyl ester.

To a stirred solution of 19.2 g (190 mM) of 2-amino-1,3,4-thiadiazole in 200 ml of acetonitrile were added in one portion 25 g (190 mM) of ethoxycarbonyl isothiocyanate. The reaction mixture was stirred at 24° C for sixteen hours. The precipitate was collected by filtration, washed three times with ethyl acetate and dried to provide 35 g (80% yield) of [(1,3,4-thiadiazol-2-ylamino)thioxomethyl]carbamic acid, ethyl ester.

Analysis calc. for $C_6H_8N_4O_2S_2$:
Theory: C, 31.02; H, 3.47; N, 24.12.
Found: C, 31.32; H, 3.27; N, 24.40.

B. Preparation of 1,3,4-thiadiazol-2-ylthiourea

A solution of 10 g of [(1,3,4-thiadiazol-2-ylamino)thioxomethyl]carbamic acid, ethyl ester (from Example 1A) in 150 ml of 1N sodium hydroxide was heated at reflux for ninety minutes. The solution was cooled and concentrated by evaporation under reduced pressure. The precipitated solid was collected by filtration and dissolved in 20 ml of water. The aqueous solution was acidified by addition of 200 ml of 1N hydrochloric acid. The product was collected by filtration and recrystallized from N,N-dimethylformamide to give 5 g of 1,3,4-thiadiazol-2-ylthiourea. m.p. 253° C.

Analysis calc. for $C_3H_4N_4S_2$:
Theory: C, 22.49; H, 2.52; N, 34.97; S, 40.02.
Found: C, 22.73; H, 2.33; N, 34.74; S, 40.26.

C. Preparation of N'-1,3,4-thiadiazol-2-ycarbamimidothioic acid, methyl ester

A mixture of 4.8 g of 1,3,4-thiadiazol-2-ylthiourea (from Example 1B) in 45 ml of 1N sodium hydroxide, 15 ml of ethanol and 4 ml of methyl iodide was heated at 40° C for ten minutes. The mixture was acidified by adding 50 ml of 1N hydrochloric acid. The reaction mixture was concentrated by evaporation under reduced pressure. The precipitated solid was collected by filtration and dried to give 3.02 g of N'-1,3,4-thiadiazol-2-ylcarbamimidothioic acid, methyl ester. m.p. 116–117° C.

Analysis calc. for $C_4H_6N_4S_2$:
Theory: C, 27.57; H, 3.47; N, 32.15; S, 36.80.
Found: C, 27.78; H, 3.55; N, 31.92; S, 36.54.

$^1$Hnmr (300 MHz) (DsDMSO/Me<Si) $\delta$ 2.42 (s, 3H, S-CHa), 8.90 (broad s, 2H, NHz) 9.08 (s, 1H, ring H) FD mass spec., parent ion 174.

D. Preparation of 1,3,4-thiadiazol-2-yl-cyanamide

A solution of 3.48 g (20 mM) of $N^1$-1,3,4-thiadiazol-2-ylcarbamimidothioic acid, methyl ester (prepared as described in Example 1C) in 200 ml of dichloromethane containing 4 g (20 mM equivalents based on 85% purity) of meta-chloroperbenzoic acid was stirred at 24° C. for two hours. The mixture was filtered and the precipitate was then stirred with 40 ml of water for two hours. The solid was collected by filtration and dried to give 1.7 g of 1,3,4-thiadiazol-2-ylcyanamide.

FD mass spec.: 126.

Analysis calc. for $C_3H_2N_4S$:
Theory: C, 28.57; H, 1.60; N, 44.42; S, 25.42.
Found: C, 28.95; H, 1.80; N, 43.60; S, 24.87.

E. Preparation of 1,3,4-thiadiazol-2-yl-cyanamide sodium salt

To a solution of 1.38 g of 1,3,4-thiadiazol-2-ylcyanamide in 10.5 ml of 1N sodium hydroxide were added 100 ml of ethanol. The mixture was filtered and the solvent was removed from the filtrate to provide an oil. The oil was crystallized from 20 ml of methanol and 100 ml of isopropyl alcohol by slowly removing the methanol by evaporation under reduced pressure to produce 980 mg of the sodium salt of 1,3,4-thiadiazol-2-ylcyanamide.

F. Preparation of 1,3,4-thiadiazol-2-yl-cyanamide-3-$\beta$-d-ribofuranose triacetate A solution of $\beta$-D-ribofuranose-1,2,3,5-tetraacetate (21 g, 66 mM) was added to 100 ml of a freshly saturated solution of dry HBr in dry methylene chloride and maintained at $-20°$ C to $-30°$ C. The reaction was kept at $-20°$ C. for 45 minutes then allowed to warm up to 0° C. very slowly. The solvent was removed under reduced pressure and the resulting syrup was co-evaporated three times with 50 ml of dry touene (the temperature of the hot bath was never allowed to go over 30° C). To the residue was then added, under Nz, a solution of the sodium salt of 1,3,4-thiadiazol-2-ylcyanamide (8.0 g, 60 mM) in 40 ml of dry DMF. The reaction was allowed to proceed overnight. Ethyl acetate (500 ml) was added and the organic layer was washed twice with sodium bicarbonate solution (200 ml), twice with 1 N HCl (200 ml) and twice with brine (200 ml). It was then dried over magnesium sulfate and the solvent removed under reduced pressure. After separation by chromatography (over silica gel in 80% ethyl acetate/hexane) the product was obtained in 75% yield.

$^1$H (NMR)(d6-DMSO) $\delta$9.02 (s, 1H, C5 H), 6.02 (d, J=2.75 Hz., 1H, 1'ribose), 5.61 (m, 1H, 2'ribose), 5.41 (m, 1H, 3'ribose), 4.40 (m, 1H, 4'ribose), 4.10–4.36 (m, 2H, 5'ribose), 2.09 (s, 3H, acetate), 2.06 (s, 3H, acetate), 2.00 (s, 3H, acetate).

$^{13}$C (NMR) (d6-DMSO) $\delta$172.5 s, 169.86 s, 169.30 s, 169.18 s, 144.1 d, 116.2 s, 87.1 d, 79.4 d, 72.9 d, 69.8 d, 62.4 t, 20.2 q, 20.2 q, 20.2 q, 20.4 q. MS-FD 384 (M+), 260, 125.

Analysis for $C_{14}H_{16}N_4O_7S$:
Calc.: C, 43.75; H, 4.20; N, 14.58; S, 8.35;
Found: C, 43.78; H, 3.99; N, 14,34; S, 8.08.

An alternative method for the preparation of 1,3,4-thiadiazol-2-ylcyanamide-3-$\beta$-D-ribofuranose triacetate is described in Example 2.

EXAMPLE 2

1,3,4-Thiadiazol-2-ylcyanamide-3-$\beta$-D-ribofuranose triacetate

A. Preparation of 1,3,4-thiadiazol-2-yl-cyanamide

1. Benzylation of 2-amino-1,3,4-thiadiazole.

A mixture of 101 9 of 2-amino-1,3,4-thiadiazole (a commercially available starting material), 650 ml of n-propanol, and 140 ml of benzyl bromide was heated in a 2 L flask. When the temperature of the reaction mixture reached 88° C., all of the 2-amino-1,3,4-thiadiazole was in solution. At 98° C. the solution began refluxing and the flask was removed from the heating mantel and placed in a water bath to control the refluxing. A 250 ml additional portion of n-propanol was added to maintain fluidity of the mixture, and the mixture was stirred for 2 hours, heating when necessary to maintain a temperature of 86° C. The mixture was then cooled to 30° C. The product, 4-imino-3-(phenylmethyl)-1,3,4-thiadiazole hydrobromide was collected, rinsed with n-propanol, and air dried. Yield 190 g (70%), m.p. 200-202° C.

2. Reaction with cyanogen bromide.

To a stirred mixture of 146 g of 4-imino-3-(phenylmethy)1,3,4-thiadiazole hydrobromide, 1 L of water, and 1 L of ethyl acetate, 44 ml of a 50% by weight solution of sodium hydroxide in water was added to dissolve the thiadiazole starting material. The aqueous layer was then separated and discarded. To the remaining ethyl acetate solution, 800 ml of water containing 84 g of sodium bicarbonate was added. To this solution was added 56.3 g of cyanogen bromide in 150 ml of ethyl acetate dropwise over 25 minutes. The mixture was stirred a further 30 minutes. Then, the aqueous layer was separated and discarded. The remaining ethyl acetate solution was washed with 200 ml of water. A saturated salt solution was added to speed separation of the layers, and the aqueous layer was then separated and discarded. The ethyl acetate solution was concentrated down to one-third of its original volume, and then 100 ml of toluene was added. This mixture was concentrated down to about one-third its original volume, and another 100 ml of toluene was added. This concentration procedure was repeated several times, producing the desired (3-phenylmethyl-1,3,4-thiadiazol-2(3H)-ylidene) cyanamide as a precipitate, which was isolated by filtration, washed with toluene and dried. Yield 57.7 g (50.6%).

3. Debenzylation

Six equivalents (7.4 g) of finely ground aluminum chloride was added to a mixture of 2.0 g of (3-phenylmethyl-1,3,4-thiadiazole-2(3H)-ylidene) cyanamide in 50 ml of methylene chloride. The mixture was stirred for 2 hours, and 50 ml of THF was added. The mixture was then poured into 50 ml of cold water, stirred for ten minutes, and filtered to remove insolubles. Then about 5 g of sodium chloride was added to the mixture to aid separation of the layers and the THF layer was separated. An additional 2 g of salt was added to the aqueous layer, and two extractions with 25 ml portions of THF were carried out. The THF layers were combined, dried with magnesium sulfate, and concentrated to a solid. A 25 ml portion of methylene chloride was added to the solid, then the solid was collected and dried, providing 0.91 g of 1,3,4-thiadiazol-2-ylcyanamide (yield 78%), which was shown to be 96.7% pure by HPLC (m.p. 155° C.).

B. Preparation of 1,3,4-thiadiazol-2-yl-cyanamide-3-β-d-ribofuranose triacetate

Utilizing the procedure of Example 1F, the desired titled product was prepared.

EXAMPLE 3

1,3,4-Thiadiazol-2-ylcyanamide-3-β-D-ribofuranose

To a solution of 2 g of 1,3,4-thiadiazole-2-ylcyanamide-β-d-ribofuranose-2,3,5-triacetate (prepared in an analogous fashion to either Example 1 or 2) in 100 ml of MeOH, were added 2 ml each of concentrated NH$_4$OH and H$_2$O. The flask was then sealed and the reaction was allowed to proceed overnight. After removal of the solvent under reduced pressure the residue was cleaned by reverse phase chromatography (C$_{18}$ column and H$_2$O). The solvent was lyophilized and the very hygroscopic product was kept under N$_2$ (50% yield). $^1$H (NMR) (D$_2$O) δ8.66 (s, 1H, 5-thiadiazole), 5.97 (d, 1H 1'-ribose), 4,82 (s, 3H, OH-ribose), 4.48 (dd, 1H, 4'-ribose), 4.31 (dd, 1H, 3'-ribose), 4.04 (m, 1H, (dd, 1H, 5'-ribose), 3.70-3.76 (dd, 1H, 5'-ribose), 3.57-3.63 (dd, 1H, 5'-ribose). FD-MS 259 (M+), 123, 126.

Analysis for C$_8$H$_{10}$N$_4$O$_4$S:
Calc.: C, 37.21; H, 3.90; N, 21.69; S, 12.42;
Found: C, 37.00, H, 4.19; N, 21.40; S, 12.15.

EXAMPLE 4

2-Amino-1,3,4-thiadiazole-3-β-D-ribofuranose

A Preparation of 2-amino-1,3,4-thiadiazole-3-β-D-ribofuranose triacetate

The desired subtitled intermediate was prepared from β-d-ribofuranose-1,2,3,5-tetraacetate and 2-amino-1,3,4-thiadiazole in an analogous fashion to that described in Example 1F to render the desired subtitled intermediate (47% yield).

$^1$H (NMR)(d6-DMSO) 68.21 (s, 1H, 5-thiadiazole H), 5.99 (d, 1H, 1'ribose, J=2.45 Hz), 5.48 (m, 1H, 2'ribose), 5.28 (m, IH, 3'ribose), 4.1-4.2 (m, 2H, 5'ribose, 4'ribose), 4.0 (m, 1H, 5'ribose), 2.05 (d, 6H, acetates), 2.00 (s, 3H, acetate).

$^{13}$C (NMR) (d6-DMSO) δ171.43, 170.84, 170.95 (acetate carbonyls) 160.02 (C-5, thiadiazole), 139.0 (C-1, thiadiazole), 87.03, 79.75, 73.84, 71.72, 64.31 (C1'-C5', ribose), 21.98, 21.92, 21.72 (acetate methyls).

B Preparation of 2-amino-1,3,4-thiadiazole-3-β-D-ribofuranose

Utilizing the procedure of Example 3, the titled compound was prepared (20 percent yield).

$^1$H (NMR)(d6-DMSO) δ8.21 (s, 1H, 5-thiadiazole), 5.65 (d, 1H, 1'ribose), 5.60 (d, 1H, 2'OH), 4.60 (t, 1H, 3'-OH), 4.30 (t, 1H, 5'-OH), 4.15 (m, 1H, 2'ribose), 3.75 (q, 1H, 3'ribose), 3.50 (m, 1H, 4'ribose), 3.30 (m, 2H, 5'ribose).

$^{13}$C (NMR) (d6-DMSO) δ159.34 (C-5, thiadiazole), 135.56 (C-2,thiadiazole), 88.04, 84.35, 72.27, 70.50, 62.34 (C-1'-C-5', ribose).

The ribosylated thiadiazoles defined above have demonstrated antiviral activity in standard tests and thus can be employed to treat or prevent diseases commonly caused by a wide range of viruses. Typical viruses against which the thiadiazoles are active include all A and B strains of influenza tested, including influenza strains such as A-Ann Arbor, A-Hong Kong, B-Great Lakes, B-Taiwan, B-Singapore, A-Brazil, A-Texas, A-Fukushina, B-Maryland and the like. Other viruses that can be controlled according to this invention include Parainfluenza, Respiratory Syncytial Viruses, the various Herpes 1 and 11 strains, Echo and Vaccinia viruses, measles and Semliki Forest.

For example, in an in vivo series of tests, groups of 15 or 30 CD-1 mice were challenged with a predetermined dose of influenza B-Great Lakes strain. A predetermined dose of the compound of Example 3 was also administered either intraperitoneally or orally, and one group that was given vehicle alone served as a control. The test continued for 10 days and the number of animals dying in each group on each day was recorded. The animals living at the end of 10 days were considered survivors. The results of this study are shown in Table 1, where Survivors are indicated as the number of animals living/the number of animals in the test group.

TABLE I

| Compound of Example 3[a] | Survivors[b] | Survivors[c] |
|---|---|---|
| 0.0 | 0/30 | 0/30 |
| 17.4 | 3/15 | 0/15 |
| 34.8 | 3/15 | 6/15 |
| 52.2 | 7/15 | 9/15 |
| 69.6 | 12/15 | 9/15 |

[a]Five doses were administered at 24, 40, 48, 64 and 72 hours at the amount shown in mg/kg
[b]Intraperitoneal administration
[c]Oral Administration Plaque-reduction studies provide a quantitative evaluation of inhibitors of virus multiplication in a tissue culture cell in vitro system. In this test, susceptible MDCK cells, were grown in 25 cm$^2$ Falcon flasks at 37° C. in Medium 199 with 5 percent inactivated fetal bovine serum (FBS), penicillin (300 units/ml) and streptomycin (300 µg/ml). When confluent monolayers were formed, growth medium was removed and 0.3 ml of an appropriate dilution of virus was added to each flask. After adsorption for one hour at room temperature, the infected cell sheet was overlaid with equal parts of 1 percent Agarose and 2×Medium 199, 2.5 percent FBS, penicillin, and streptomycin. Varying concentrations of the compound of Example 3 were incorporated in the agar overlay. The compounds were dissolved in dimethyl sulfoxide (DMSO) at a concentration of 10,000 µg/ml and then an aliquot was diluted to the desired concentration with the agar medium mixture. Flasks were incubated until control flasks indicated optimum plaque size (2–10 mm). A solution containing 10 percent formalin and 2 percent sodium acetate was added to each flask to inactivate the virus and fix the cell sheet to the plastic surface. The plaques were counted after staining the surrounding cell areas with crystal violet. Results from duplicate flasks at each concentration were averaged and compared with control flasks. The inhibition of plaque formation by 50 percent (IC$_{50}$) was estimated by plotting all results from 10 to 90 percent inhibition. The results of this plaque reduction assay showed IC$_{50}$ values (in mcg/ml) of 2.8 for influenza Brazil A; and 10.5 for influenza Great Lakes B.

Utilizing the above plaque-reduction study, the compound of Example 4 exhibited an IC$_{25}$ (i.e., inhibition of plaque formation by 25 percent) of 28 for influenza Brazil A (reported in mcg/ml).

The preferred manner of using the compounds is for in vivo use, whereby the compounds can be administered either parenterally, topically, orally, by inhalation or the intranasal route to a mammal suffering from a viral infection or susceptible thereto. For parenteral administration, as by the intraperitoneal route, the compound may be dissolved or suspended in water containing 2% of a surface active agent, particularly an emulphor (a polyhydroxylated fatty acid). Oral administration is, of course, preferred. For such use, a compound as defined herein is mixed with one or more standard pharmaceutically acceptable diluents, excipients or carriers such as starch, sucrose, lactose, calcium carbonate, etc., and the mixture loaded into empty telescoping gelatin capsules such that each capsule contains an amount of a compound of the present invention effective to suppress the growth of the virus, either prospective or present. In other words, the compounds can be used prophylactically or as therapeutic agents. Alternatively, one or more compounds of the invention can be mixed with various excipients including starch, lubricating agents, wetting agents, etc., such as stearic acid, magnesium stearate and the like, and the mixture pressed into tablets, each tablet containing an amount of the drug effective to abort or cure an attack of influenza or other virus. Such tablets can be scored so as to provide half or quarter dosages where the drug is to be administered to children. The compounds can also be administered in solution or suspension.

To practice the antiviral method of this invention, all that is required is that an effective antiviral amount of a thiadiazole antiviral agent be administered to an animal suffering from or susceptible to a viral infection. The compounds will ideally be formulated with pharmaceutically acceptable diluents for convenient administration, for example orally, topically or parenterally, and can be employed for prophylatic as well as therapeutic treatment. The formulations will normally contain from about 1 to about 95 percent by weight of active thiadiazole antiviral agent.

For oral administration, the compounds will be formulated with common diluents and excipients such as sucrose, starch, microcrystalline cellulose, acacia and the like, and molded into tablets or pills or encapsulated into gelatin capsules, or formulated as solutions, elixirs, lozenges or the like. Topical formulations will include mixing the thiadiazole antiviral agent with excipients such as beeswax, lanolin, oil and the like for ready formulation as ointments, salves, creams, tinctures, lotions, patches and the like.

For severe viral infections, the antiviral thiadiazoles will be formulated for intravenous or intramuscular administration. Such formulations will contain from about 1 to about 50 percent active agent (i.e., one or more compounds of the invention). The compounds will be dissolved in common diluents such as isotonic saline or dextrose solutions, for intravenous infusion, and can be dissolved in polyhydric aliphatic alcohols such as propylene glycol or polyethylene glycol for easy intravenous or intramuscular injection.

Pharmaceutically acceptable salts can be prepared from those compounds which are sufficiently acidic or basic to react with common organic and inorganic acids and bases such as hydrochloric acid, succinic acid, sodium hydroxide, and the like. The pharmaceutically acceptable salts generally have enhanced solubility characteristics compared to the compound from which they are derived, and thus are often more amenable to formulation as liquids or emulsions.

The 3-ribosylated thiadiazole antiviral agents described herein are active over a wide range of dose levels. While the particular dose to be administered will be determined by the precise viral infection to be treated or guarded against and its severity, the route of administration, and related circumstances that will be determined by attending medical practitioners, the normal effective antiviral amount will range from about 0.1 to about 100 mg/kg, and more typically about 0.5 to about 25 mg/kg.

In a preferred method of treatment, the ribosylated thiadiazole compounds are administered to mammals susceptible to infection with influenza virus including horses, mice, pigs and humans. Among humans, the compounds are administered prophylactically particularly to the elderly, young children, nurses, doctors, and other hospital or public health personnel, for example when there is evidence of an imminent influenza epidemic. The compounds can also be given to anyone having a known exposure to a person with influenza. It is a particular advantage of the therapeutic processes of this invention that the compounds may be administered either prophylactically or therapeutically to patients without a preliminary determination that the virus is influenza virus A strain or B strain, since the compounds are effective against both strains.

The following Examples illustrate some typical formulations using compounds of Formula 1.

EXAMPLE 5

| Preparation of Tablets | |
|---|---|
| The compound of Example 3 | 100 mg. |
| Lactose | 200 mg. |
| Corn Starch | 300 mg. |
| Corn Starch Paste | 50 mg. |
| Calcium Stearate | 5 mg. |
| Dicalcium Phosphate | 45 mg. |

The active ingredient (i.e., the compound of Example 3), corn starch, lactose and dicalcium phosphate are uniformly blended. The corn starch paste is prepared as a 10 percent aqueous paste and is blended into the mixture to uniformity. The mixture is blended with the calcium stearate and then compressed into a tablet.

EXAMPLE 6

| Preparation of Suppositories | |
|---|---|
| The compound of Example 4 | 500 mg. |
| Theobromo oil | 1500 mg. |

The above ingredients are blended to uniformity at a temperature of about 60° C. and then cooled in a tapered mold.

EXAMPLE 7

| Preparation of Oral Suspension | |
|---|---|
| The compound of Example 3 | 500 mg. |
| Sorbitol solution (70% N.F.) | 40 mg. |
| Sodium benzoate | 150 mg. |
| Lactose | 10 mg. |
| Cherry flavor | 50 mg. |
| Ethanol | 100 ml. |

The above ingredients are combined such that each ml. of syrup contains 5 mg. of active ingredient. Administration of about 5 to about 20 ml. of the syrup each day will protect a human subject from viral infections such as influenza.

EXAMPLE 8

| Intransal Formulation | |
|---|---|
| | % by weight |
| The compound of Example 4 | 1.0 |
| Antarox (non-ionic polyoxyethylated fixed oil, GAF Corp.) | 38.5 |
| Ethanol | 10.0 |
| Freon 11 (trichloromonofluoromethane) | 25.0 |
| Freon 12 (dichlorodifluoromethane) | 25.0 |
| Menthol | 0.5 |

The active ingredient is added to the Antarox at about 70-80° C. and the mixture is stirred until a solution is formed. The solution is cooled and diluted with a mixture of the menthol in the ethanol. The resulting solution is placed in an aerosol container and chilled to 0° C., and the Freon propellants are added and the aerosol container is sealed with a valve.

We claim:

1. A compound of the formula:

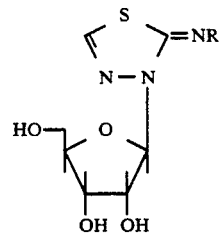

wherein:
R is hydrogen, —CN,

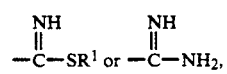

where $R^1$ is $C_1$–$C_6$ alkyl, cyano-$C_1$–$C_4$ alkyl or pyridyl-$C_1$–$C_4$ alkyl, or a pharmaceutically acceptable salt thereof.

2. The compound of claim 1 which is 1,3,4-thiadiazol-2-ylcyanamide-3-β-D-ribofuranose.

3. The compound of claim 1 which is 2-amino-1,3,4-thiadiazole-3-β-D-ribofuranose.

4. An antiviral method which comprises administering to a mammal which has a virus selected from the group consisting of the various A and B strains of influenza, Parainfluenza, Respiratory Syncytial Virus, the various strains of Herpes I and II, ECHO, Vaccinia, measles and Semliki Forest, an effective antiviral amount of a compound of the formula:

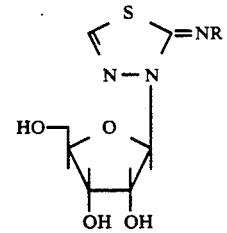

wherein:
R is hydrogen, —CN,

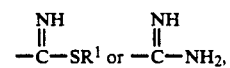

where $R^1$ is $C_1$–$C_6$ alkyl, cyano-$C_1$–$C_4$ alkyl or pyridyl-$C_1$–$C_4$ alkyl, or pharmaceutically acceptable salt thereof.

5. The method of claim 4 in which the compound employed is 1,3,4-thiadiazol-2-ylcyanamide-3-β-D-ribofuranose.

6. The method of claim 4 in which the compound employed is 2-amino-1,3,4-thiadiazole-3-β-D-ribofuranose.

7. A pharmaceutical formulation comprising an effective amount of a compound of the formula

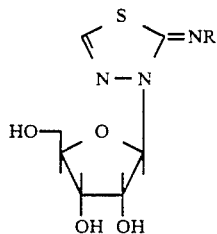

wherein:

R is hydrogen, —CN,

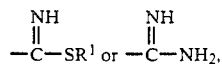

where $R^1$ is $C_1$–$C_6$ alkyl, cyano-$C_1$–$C_4$ alkyl, or pyridyl-$C_1$–$C_4$ alkyl, or a pharmaceutically acceptable salt thereof in association with one or more pharmaceutically acceptable diluents, excipients or carriers.

8. The formulation of claim 7 in which the compound employed is 1,3,4-thiadiazol-2-ylcyanamide-3-β-D-ribofuranose.

9. The formulation of claim 7 in which the compound employed is 2-amino-1,3,4-thiadiazole-3-β-D-ribofuranose.

* * * * *